(12) United States Patent
Wolff et al.

(10) Patent No.: US 9,248,084 B2
(45) Date of Patent: Feb. 2, 2016

(54) CLEANING COMPOSITION HAVING IMPROVED SOIL REMOVAL

(71) Applicant: KIMBERLY-CLARK WORLDWIDE, INC., Neenah, WI (US)

(72) Inventors: Kelly Laura Wolff, Appleton, WI (US); Christopher V. Decker, Neenah, WI (US); Scott W. Wenzel, Neenah, WI (US); Corey Thomas Cunningham, Larsen, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 13/839,881

(22) Filed: Mar. 15, 2013

(65) Prior Publication Data

US 2014/0274851 A1   Sep. 18, 2014

(51) Int. Cl.

| | |
|---|---|
| *C11D 1/66* | (2006.01) |
| *C11D 3/20* | (2006.01) |
| *A61Q 19/00* | (2006.01) |
| *A61K 8/39* | (2006.01) |
| *A61K 8/33* | (2006.01) |
| *A61Q 19/10* | (2006.01) |

(52) U.S. Cl.
CPC ... *A61K 8/39* (2013.01); *A61K 8/33* (2013.01); *A61Q 19/10* (2013.01); *A61K 2800/30* (2013.01)

(58) Field of Classification Search
CPC .......... C11D 1/66; C11D 3/20; C11D 3/2068; C11D 7/263; A61Q 19/00
USPC ......... 510/128, 137, 159, 421, 432, 475, 505; 424/70.31
See application file for complete search history.

(56) References Cited

U.S. PATENT DOCUMENTS

| | | | |
|---|---|---|---|
| 4,100,324 A | | 7/1978 | Anderson et al. |
| 5,284,703 A | | 2/1994 | Everhart et al. |
| 5,350,624 A | | 9/1994 | Georger et al. |
| 5,585,104 A | | 12/1996 | Ha et al. |
| 5,786,319 A | | 7/1998 | Pedersen et al. |
| 5,877,133 A | | 3/1999 | Good |
| 5,980,924 A | * | 11/1999 | Yamazaki et al. ............ 424/402 |
| 6,197,734 B1 | | 3/2001 | Vlasblom |
| 6,228,830 B1 | | 5/2001 | Vlasblom |
| 6,495,508 B1 | * | 12/2002 | Leonard et al. ............... 510/438 |
| 6,511,546 B1 | | 1/2003 | Bivins et al. |
| 2004/0136943 A1 | | 7/2004 | Tomokuni |
| 2010/0120646 A1 | | 5/2010 | Leroy |
| 2011/0319312 A1 | | 12/2011 | Schwerter et al. |

FOREIGN PATENT DOCUMENTS

| | | | | |
|---|---|---|---|---|
| GB | 2407817 | * | 5/2005 | ............ C11D 17/04 |
| WO | 2012170841 A1 | | 12/2012 | |

OTHER PUBLICATIONS

International Search Report and Written Opinion for PCT/IB2014/059003, mailed May 27, 2014.

\* cited by examiner

*Primary Examiner* — Brian P Mruk (57) ABSTRACT

Cleaning compositions including a non-ionic surfactant and a glycol ether are disclosed. These cleaning compositions are useful as liquid cleaners or de-greasers for animate surfaces, such as skin. The cleaning compositions provide improved cleaning and removal of soils without the use of certain VOCs.

20 Claims, 3 Drawing Sheets

CLEANING COMPOSITION HAVING IMPROVED SOIL REMOVAL

BACKGROUND OF THE DISCLOSURE

The present disclosure relates generally to a cleaning composition including one or more non-ionic surfactants and a glycol ether. The combination of a non-ionic surfactant and a glycol ether provides improved grease removal on animate surfaces, and in particular, skin. Accordingly, the cleaning compositions of the present disclosure are useful as skin cleaning compositions such as used in liquid hand soaps, as well as for inclusion in cleansing personal products such as cleaning wipes.

Conventional detergent cleansers for soil removal have included volatile organic compounds (VOCs). Many high VOC content materials are excellent solvents and possess excellent cleaning properties. For example, d-limonene has proven to be a powerful solvent; thereby, providing a significant cleaning benefit. In recent years, however, stringent restrictions on the amounts and types of these materials that can be emitted into the atmosphere have been imposed. Although not specifically considered hazardous air pollutants, VOCs are thought to contribute to the overall lowering of air quality.

Accordingly, there is a need for cleaning compositions and cleansing products including the cleaning compositions that provide effective skin cleaning and skin degreasing without the use of VOCs. It would further be advantageous if the cleaning compositions were phase stable.

BRIEF DESCRIPTION OF THE DISCLOSURE

It has now been unexpectedly found that improved animate cleaning compositions effective for cleaning and degreasing skin can be formed with the use of a combination of one or more non-ionic surfactants and a glycol ether. More particularly, the animate cleaning compositions of the present disclosure effectively clean and degrease skin without the use of d-limonene.

Accordingly, the present disclosure is directed to an animate cleaning composition comprising a non-ionic surfactant and a glycol ether. The composition has a surface cleaning index of from greater than 0 to 5 or less.

The present disclosure is further directed to a cleaning composition comprising a non-ionic surfactant and a glycol ether. The non-ionic surfactant is present in an amount of less than 6% by weight of the composition. The composition has a surface cleaning index of from greater than 0 to 5 or less, and has a pH of from about 3 to about 8.

The present disclosure is further directed to a wipe comprising a fibrous substrate and a cleaning composition. The composition comprises a non-ionic surfactant and a glycol ether, and has a surface cleaning index of from greater than 0 to 5 or less.

Other objects and features will be in part apparent and in part pointed out hereinafter.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DEFINITIONS

Within the context of this specification, each term or phrase below will include, but not be limited to, the following meaning or meanings:

As used herein, "animate surface" refers to any surface or interface in or on the body, such as human skin.

As used herein, "liquid composition" or "liquid formulation" refers to both liquid and gel compositions. Non-limiting examples of liquid cleaning compositions of the present disclosure include wet wipe solutions, body cleansers, hair shampoos, and the like.

As used herein, "soil" refers to any medium that stains or contaminates a substrate; including grease, oil (e.g., oil-based ink, oil-based paint, engine oil), tar, grime, latex paint, and the like as known in the art.

As used herein, "surface cleaning index (SCI)" refers to the weight ratio of non-ionic surfactant to glycol ether solvent in the cleaning composition.

As used herein, "phase stable" refers to a composition that does not separate into separate phases after a period of at least about 2 weeks in room temperature.

DETAILED DESCRIPTION OF THE DISCLOSURE

The present disclosure is directed to an animate cleaning composition including one or more non-ionic surfactants and a glycol ether. The cleaning composition provides effective cleaning of animate surfaces, and, in particular, of human skin, without the use of VOCs that may be a contributing factor in low air quality. In particular, the animate cleaning composition is particularly useful as a skin degreaser. As described more fully herein, the cleaning compositions of the present disclosure provide synergistic cleaning results to animate surfaces as compared to the non-ionic surfactants or glycol ethers used alone.

The cleaning compositions of the present disclosure include one or more non-ionic surfactants. Suitable examples of non-ionic surfactants for use in the present disclosure include, but are not limited to, alcohol ethoxylates, including Guebert alcohol ethoxylates (e.g., $C_{10}$ Guebert alcohols with 3-8 moles of ethylene oxide) such as Lutensol XP (BASF, Germany); $C_9$-$C_{11}$ alcohols with 2.5-6 moles of ethylene oxide such as Tomadol 91-6 (Air Products and Chemicals, Inc., Allentown, Pa.); alkaline oxide adducts of polyhydric components; alkyl aryl ethoxylates; alcohol ethoxylates and combinations thereof. Particularly suitable non-ionic surfactants typifying the alkalene oxide adducts of polyhydric components are the ethylene oxide adducts of ethylene diamine sold commercially under the name Tetronic (BASF, Germany), as well as the ethylene oxide propylene oxide adducts of propylene glycol commercially sold under the name Pluronic (BASF, Germany).

Suitable alcohol ethoxylates for use in the cleaning compositions of the present disclosure include the condensation products of aliphatic alcohols with ethylene oxide. The alkyl chain of the aliphatic alcohol may either be straight or branched and generally contains 8-22 carbon atoms. Examples of commercially available non-ionic surfactants of this type include Genupol UD 079 (a branched chain alcohol ethoxylate with 3-7 ethylene oxide groups and a $C_{11}$) (Clariant, Switzerland) and Tergitol 15S3 (The Dow Chemical Company, Midland, Mich.). Linear primary alcohol ethoxylates are particularly suitable in the cleaning compositions of the present disclosure. Such linear primary alcohol ethoxylates can have an alcohol chain of from $C_6$-$C_{13}$ with 2.5 to 9 ethylene oxide groups per molecule, and including 2.5 to 6 ethylene oxide groups per molecule. One particularly suitable non-ionic surfactant is Tomadol 91-6 (Air Products and Chemicals, Inc., Allentown, Pa.) (also referred to as Neodol 91-6 (Shell Chemicals, Houston, Tex.)), which has a $C_9$-$C_{11}$ primary alcohol chain with approximately 6 ethylene oxide groups per molecule.

In addition, suitable alkyl aryl ethoxylates for use in the cleaning composition of the present disclosure include, for example, ethoxylated alkylphenols. The alkyl substituent in such compounds may be derived from polymerized propylene, diisobutylene, octene or nonene. Examples of compounds of this type include nonylphenol condensed with 2 to 9 moles of ethylene oxide per mole of nonylphenol and dodecylphenol condensed with up to 10 moles of ethylene oxide per mole of phenol, and octylphenols condensed with 5-12 ethylene oxide molecules per mole of phenol. Commercially available non-ionic surfactants of this type include Tergitol NP-9 available from Union Carbide (Houston, Tex.), Igepal CO-530 available from Solvay Novecare (Bristol, Pa.), and Triton X-45 and X-114 available from Union Carbide (Houston, Tex.).

The non-ionic surfactants for use in the cleaning compositions of the present disclosure include those having an HLB value of from about 6 to about 13, including from about 8 to about 12.5, and including from about 10 to about 12.5. It has been surprisingly found that non-ionic surfactants having HLB values of from between about 6 to about 13 have improved cleaning properties as these non-ionic surfactants adequately interact with hydrophobic soils and effectively disperse the hydrophobic soils into the bulk phase of the cleaning composition, which as described below, typically includes water as a major component.

Typically, the cleaning compositions of the present disclosure include the non-ionic surfactant in amounts of less than 6% by total weight of the cleaning composition, including 5% or less by total weight of the cleaning composition, including 4% or less by total weight of the cleaning composition, including 3% or less by total weight of the cleaning composition, including 2% or less by total weight of the cleaning composition, and including 1% or less by total weight of the cleaning composition. In suitable embodiments, the cleaning composition includes from about 0.5% by total weight to about 5% by total weight of the non-ionic surfactant, including from about 1% by total weight to about 4% by total weight of the non-ionic surfactant, including from about 2% by total weight to about 4% by total weight of the non-ionic surfactant, and including about 3% by total weight of the non-ionic surfactant. It should be understood in the art that as one or more non-ionic surfactants can be used in the present cleaning compositions, the total amount of non-ionic surfactants in the cleaning compositions includes less than 6% by total weight of the cleaning composition, including 5% or less by total weight of the cleaning composition, including 4% or less by total weight of the cleaning composition, including 3% or less by total weight of the cleaning composition, including 2% or less by total weight of the cleaning composition, and including 1% or less by total weight of the cleaning composition. In some embodiments, the total amount of non-ionic surfactants in the cleaning compositions includes from about 0.5% by total weight to about 5% by total weight non-ionic surfactant, including from about 1% by total weight to about 4% by total weight non-ionic surfactant, including from about 2% by total weight to about 4% by total weight non-ionic surfactant, and including about 3% by total weight non-ionic surfactant.

The cleaning compositions of the present disclosure also include one or more glycol ethers in combination with the non-ionic surfactant. Suitable glycol ethers for use in the cleaning composition of the present disclosure include, but are not limited to, propylene glycol methyl ether, dipropylene glycol methyl ether, tripropylene glycol methyl ether, propylene glycol methyl ether acetate, dipropylene glycol methyl ether acetate, propylene glycol n-butyl ether, dipropylene glycol n-butyl ether, tripropylene glycol n-butyl ether, ethylene glycol phenyl ether, ethylene glycol n-butyl ether, diethylene glycol n-butyl ether, trimethylene glycol n-butyl ether, diethylene glycol methyl ether, trimethylene glycol methyl enantiomer, and combinations thereof.

The cleaning compositions of the present disclosure include the glycol ethers in amounts of less than 30% by total weight of the cleaning composition, including less than 20% by total weight of the cleaning composition, including less than 15% by total weight of the cleaning composition, including less than 10% by total weight of the cleaning composition, including from about 0.5% by total weight of the cleaning composition to about 6% by total weight of the cleaning composition, including from about 1% by total weight of the cleaning composition to about 5% by total weight of the cleaning composition, including from about 2% to about 4% by total weight of the cleaning composition, and including about 3% by total weight of the cleaning composition.

In addition, to provide the improved cleaning benefit, the weight ratio of non-ionic surfactant to glycol ether is suitably 5:1 or less, including between greater than 0:5 to 5:1 or less, including from greater than 0:2 to 5:1 or less. Suitable embodiments include a weight ratio of non-ionic surfactant to glycol ether of from about 0.01:5 to 5:1, from about 0.1:5 to 5:1, from about 0.2:4 to about 4:1; from about 0.5:3.5 to about 3.5:1, from about 1:3 to about 3:1, from about 1:2 to about 2:1, and about 1:1.

As noted above, these weight ratios can be further defined as the surface cleaning index (SCI) of the cleaning composition. Accordingly, the cleaning composition can include a SCI of 5 or less, including between greater than 0 to 5 or less, including from about 0.002 to 5, including from about 0.02 to 5, including from about 0.05 to about 4, including from about 0.2 to about 3.5, including from about 0.33 to about 3, including from about 0.5 to about 2, and including about 1.

In particularly suitable embodiments, the cleaning composition is in the form of a liquid composition including water in an amount of from about 65% to about 95% by total weight of the cleaning composition, including from about 70% to about 95% by total weight of the cleaning composition, and including from about 80% to about 90% by total weight of the cleaning composition.

Other suitable solvents for use in the cleaning composition may include those known in the art, for example, one or more non-aqueous solvents including, but not limited to, glycerin, glycols (in addition to the glycol ethers described above, including propylene glycol, butylene glycol, triethylene glycol, hexylene glycol, ethoxydiglycol, and dipropyleneglycol), short chain alcohols (e.g., ethanol, etc.), and combinations thereof. Although not required, non-aqueous solvents may aid in dissolving certain components (e.g., preservatives, etc.).

In one suitable embodiment, the cleaning composition includes a solvent, and in particular, water, in an amount such that the viscosity of the cleaning composition is from about 1 cps to about 100,000 cps, including from about 1,000 cps to about 75,000 cps, and including from about 5,000 cps to about 50,000 cps. In one embodiment, the cleaning composition is a lotion composition having a viscosity of from about 5,000 cps to about 50,000 cps. In another embodiment, the cleaning composition is a gel composition having a viscosity of about 25,000 cps. In yet another embodiment, the cleaning composition is for use with a wipe, such as described below, and has a viscosity of about 1 cps.

In some embodiments, the cleaning composition may also include various optional agents to modify the physical, chemical, hedonic or processing characteristics of the compositions or serve as beneficial agents when used for a targeted purpose or in a targeted user population. The optional agents include, for example, water-soluble emollients, humectants, moisturizers, botanicals, vitamins, preservatives, pH modifiers, sequestrants, thickeners, antioxidants, anti-reddening agents, astringents, deodorants, external analgesics, film formers, fragrances, hydrotropes, skin conditioning agents, skin exfoliating agents, skin protectants, and the like.

Generally, water-soluble emollients lubricate, soothe, and soften the skin surface. Exemplary water-soluble emollients include ethoxylated or propoxylated oily or waxy ingredients such as esters, ethers, fatty alcohols, hydrocarbons, lanolin, and the like, and combinations thereof. Particular water-soluble emollients could include, but are not to be limited to, PEG-7 glyceryl cocoate, PEG-6 caprylic/capric glycerides, hydrolyzed jojoba esters, the Hydramol™ product line from Lubrizol Corporation (Wickliffe, Ohio), the Resplanta® line of products from Res Pharma (Italy), and the like. One skilled in the art will recognize that this list is not all inclusive and could include any other suitable materials commonly known in the art or referenced in the Personal Care Products Council (PCPC) Compilation of Ingredients Used in Cosmetics in the United States (CIUCUS).

Humectants are hydroscopic agents that are widely used as moisturizers. Their function is to prevent the loss of moisture from the skin and to attract moisture from the environment. Common humectants include, for example, glycerin, propylene glycol, butylene glycol, betaine, sodium hyaluronate, sorbitol, urea, hydroxyethyl urea, and the like, and combinations thereof.

Furthermore, the composition may include foam builders, such as, cocamidopropyl PG-dimonium chloride phosphate, lauramidopropyl PG-dimonium chloride, meadowfoamamidopropyl PG-dimonium chloride, myristamidopropyl PG-dimonium chloride phosphate, palmitamidopropyltrimonium chloride, sodium cocoamphoacetate, disodium cocoamphodiacetate, and combinations thereof.

Preservatives for increasing the shelf life of the compositions may also be used. Exemplary suitable preservatives include, but are not limited to, Kathon™ CG, which is a mixture of methylchloroisothiazolinone and methylisothiazolinone, available from The Dow Chemical Company, Midland, Mich.; Mackstat® H 66, available from Rhodia, member of the Solvay Group, Bristol, Pa.; DMDM hydantoin (e.g., Glydant® Plus, Lonza, Inc., Switzerland); tetrasodium EDTA; iodopropynyl butylcarbamate; benzoic esters (parabens), such as methylparaben, propylparaben, butylparaben, ethylparaben, sodium methylparaben, and sodium propylparaben; phenoxyethanol; benzyl alcohol; phenethyl alcohol; 2-bromo-2-nitropropane-1,3-diol; benzoic acid; amidazolidinyl urea; diazolidinyl urea; sodium benzoate; phenoxyethanol; and the like. Other suitable preservatives include those sold by Ashland Inc., Ashland, Ky., such as "Germall 115" (amidazolidinyl urea), "Germall II" (diazolidinyl urea), and "Germall Plus" (diazolidinyl urea and iodopropynyl butylcarbonate). Particularly suitable preservatives include Neolone™ CapG, which is a mixture of methylisothiazolinone and caprylyl glycol, available from Dow Chemical Company, Midland, Mich.; Symdiol® 68, which is a mixture of 1,2-hexanediol and caprylyl glycol, available from Symrise, Teterboro, N.J.; and Lexgard® O, which is caprylyl glycol, available from Inolex Chemical Company, Philadelphia, Pa.

Suitable skin conditioning agents for use in the cleaning compositions include skin conditioning agents known in the art. Particularly suitable skin conditioning agents include, for example, hydrolyzed plant proteins such as hydrolyzed wheat protein, hydrolyzed soy protein, hydrolyzed collagen, and the like.

In general, the pH of the cleaning compositions may be controlled to be within any desired range, depending on the targeted use. By way of example, for cleaning of an animate surface, such as removing grease from skin, it is typically desirable to have a cleaning composition with a slightly acidic to neutral pH, such as from about 3 to about 8, including from about 4 to about 7.5, and including from about 4.5 to about 7. If necessary, various pH modifiers may be utilized in the cleaning composition to achieve the desired pH level. For instance, some examples of basic pH modifiers that may be used in the compositions of the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; sodium citrate; monoethanolamine; triethylamine; isopropanolamine; diethanolamine; and triethanolamine.

Moreover, some examples of acidic pH modifiers that may be used in the compositions of the present disclosure include, but are not limited to, mineral acids; carboxylic acids; and polymeric acids. Specific examples of suitable mineral acids are hydrochloric acid, nitric acid, phosphoric acid, and sulfuric acid. Specific examples of suitable carboxylic acids are acetic acid, tartaric acid, citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include carrageenic acid, humic acid, fulvic acid, and alginic acid.

In one embodiment, the cleaning composition may additionally include one or more sequestrants. A sequestrant is a substance whose molecules can form one or more bonds with a metal ion. In particular, water that may be contained in the cleaning composition often contains metal ions, such as calcium ions, that might react with anionic components (e.g., acids) present within the cleaning composition. For example, in one embodiment, an anionic component that remains substantially unreacted with metal ions can better function as a cleansing agent. Some examples of sequestrants that may be used in the cleaning compositions of the present disclosure include, but are not limited to, ethylenediamines, ethylenediaminetetraacetic acids (EDTA) acid and/or salts thereof, citric acids and/or salts thereof, glucuronic acids and/or salts thereof, iminodisuccinic acid and/or salts thereof, polyphosphates, organophosphates, dimercaprols, and the like.

Suitable thickeners for use in the cleaning compositions of the present disclosure include thickeners such to build the viscosity of the cleaning composition as described above to prevent run off of the cleaning composition when in use. Suitable examples of thickeners include, for example, acrylates (e.g., Carbopol Ultrez 10 Polymer, The Lubrizol Corporation (Wickliffe, Ohio)), gums, cellulosics, starches, polyethylene glycols (e.g., PEG-120 methyl glucose dioleate, PEG-120 methyl glucose triisostearate, PEG-120 methyl glucose trioleate, PEG-150 distearate, PEG-175 diisostearate, and other high molecular weight PEGs (e.g., PEG-1000)), and combinations thereof.

In addition, the cleaning compositions of the present disclosure can further include one or more surfactants in addition to the non-ionic surfactant described above. Suitable additional surfactants include anionic, cationic, and amphoteric surfactants as known in the cleaning art. It should be understood that the additional surfactants should be compatible with the cleaning compositions of the present disclosure. Particularly suitable additional surfactants include amine oxide surfactants such as Mackamine LO, Mackamine C-8, and Mackamine C-10 (all available from Rhodia, member of the Solvay Group, Bristol, Pa.).

Still other optional agents include: antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); botanicals (e.g., Actiphyte of Aloe Vera 10 Fold GL, Actiphyte of Cucumber GL, Actiphyte of Japanese Green Tea GL, all from The Lubrizol Corporation, Wickliffe, Ohio); vitamins (e.g., tocopheryl acetate, retinyl palmitate, panthenol, ascorbic acid); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal); hydrotropes; and skin protectants (a drug product which protects injured or exposed skin or mucous membrane surface from harmful or annoying stimuli).

The amounts of the optional components will depend on the composition to be prepared and the amounts of the other components in the cleaning composition.

The cleaning compositions of the present disclosure are substantially free of d-limonene. In this context, and unless otherwise specified, the term "substantially free" means that the cleaning compositions contain less than a functional amount of d-limonene, typically less than 1%, including less than 0.5%, including less than 0.1%, including less than 0.05%, including less than 0.015%, including less than 0.001%, and also including zero percent, by total weight of the cleaning composition.

Methods of Preparing the Compositions

The cleaning compositions are generally prepared by mixing all components together to form a homogeneous solution. Typically, in one embodiment, the cleaning composition is prepared by: mixing any solid components (e.g., thickeners) with water until hydrated to prevent clumping; adding the non-ionic surfactant to the mixture; adding the glycol ether; adding any additional components; and then adjusting the pH to the desired final pH of from about 3 to about 8. In another embodiment, the cleaning composition is prepared by: first mixing the glycol ether and the non-ionic surfactant; then adding any additional desired components into the mixture; adding water; and then adjusting the pH to the desired final pH of from about 3 to about 8.

While used as a liquid composition, any solid components are first completely dissolved in water or other solvents before mixing with other components. In addition, the liquid composition may be used as a lotion, gel or rinse or may be applied to a substrate to form a wet or dry wipe.

Cleansing Products Including the Cleaning Composition

While capable of being applied directly to an animate surface, and suitably skin, such as in the form of a lotion, gel, spray, rinse, or the like, in some embodiments, the cleaning compositions may be applied to one or more substrates to provide for a cleansing product, such as a wipe, wrap (e.g., medical wraps and bandages), and the like. Wipes including the cleaning composition can be wet wipes or dry wipes. As used herein, the term "wet wipe" means a wipe that includes greater than 70% (by weight substrate) moisture content. As used herein, the term "dry wipe" means a wipe that includes less than 10% (by weight substrate) moisture content. Specifically, suitable wipes for including the cleaning composition can include wet wipes, hand wipes, face wipes, cosmetic wipes, and the like. Particularly preferred wipes are wet wipes, such as hand wipes.

Materials suitable for the substrate of the wipes are well known to those skilled in the art, and are typically made from a fibrous sheet material which may be either woven or nonwoven as described more fully in U.S. Pat. No. 4,100,324, issued to Anderson, et al. (Jul. 11, 1978); U.S. Pat. No. 5,284,703, issued to Everhart, et al. (Feb. 8, 1994); and U.S. Pat. No. 5,350,624, issued to Georger, et al. (Sep. 27, 1994), which are incorporated by reference to the extent to which they are consistent herewith.

Typically, when used with a substrate material, the cleansing products include the cleaning composition in an add-on amount of from about 150% by weight to about 600% by weight dry basesheet, including from about 175% by weight to about 450% by weight dry basesheet, and including from about 200% by weight to about 400% by weight dry basesheet.

Methods of Use

The cleaning compositions of the present disclosure can be used to provide effective cleansing of animate surfaces, and in particular, of human skin. In one embodiment, the cleaning compositions may be used to remove grease or other debris from a user's body.

Moreover, the cleaning compositions provide a cleaning or de-greasing effect without the use of undesirable components such as d-limonene. Accordingly, the user can effectively clean or de-grease the body without the use of potentially undesirable components.

The cleaning compositions have improved phase stability such that the cleaning compositions retain a cleaning or de-greasing effect for a sufficiently long period of time in order to effectively remove grease and other debris from the animate surface.

Having described the disclosure in detail, it will be apparent that modifications and variations are possible without departing from the scope of the disclosure defined in the appended claims.

EXAMPLES

The following non-limiting Examples are provided to further illustrate the present disclosure.

Example 1

In this Example, the cleaning ability of suitable cleaning compositions of the present disclosure was analyzed.

Tiles (available as Armstrong Imperial Texture, Standard Excelon Vinyl Composition Tile (Pattern 51899) from Home Depot) were cut in the direction of the grain into strip samples of 3"×12". Using a reflectometer (available as Photovolt 577A, from Photovolt Instruments, Minneapolis, Minn.), unsoiled measurements of the tile samples ("clean" tiles) were taken to provide the "clean" surface reflectance. The samples were then treated with either 0.15 g modified gear grease (MGG) (including 96% by weight Valvoline Moly Fortified Multi-purpose Grease from Advance Auto Parts and 4% by weight carbon black), or approximately 0.02 to 0.03 g oil-based ink (OBI) (available as CML-Oil Base Plus VS710-Pantone Black, from Royal Dutch Printing Ink Factories Van Son, Hilversum, Holland) as the soil. To prepare the tile samples, the rough side of the tile was placed face up and four 3"×2" squares were measured out on each tile sample for application of the soil.

To apply the MGG, the tile sample was placed on a scale, the scale was tared, and the MGG was applied to the surface by contacting the sample directly with the MGG on the scale. For the OBI, a weight boat, containing the OBI and a spatula, is tared, and the OBI was applied to the sample with the spatula.

Figure 1:
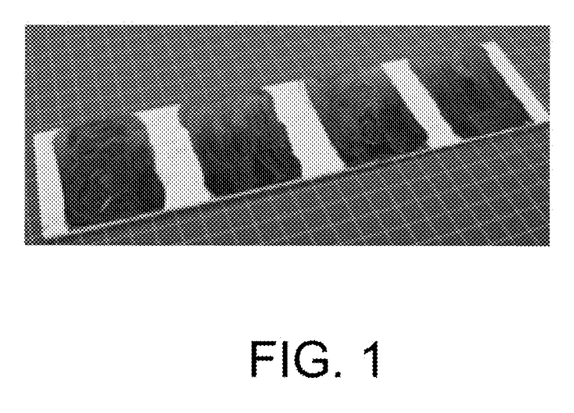
FIG. 1 depicts the smearing of soil onto the tile samples as described in Example 1.

Prior to smearing the specified soil to cover the 3"×2" square, gloved fingers were pre-soiled by dabbing one finger in the soil to be tested and then rubbing the soil over the finger and removing excess soil with a paper towel. Pre-soiling the finger helped to prevent soil transfer loss when smearing the soil on the tile sample. Using the pre-soiled finger, the soil was then smeared to cover the 3"×2" square. After soiling, the tile sample should look similar to FIG. 1. The soil samples were then allowed to dry overnight. After drying, the percent soiled in two spots of each square was measured with the reflectometer ("soiled tile" measurements).

Various cleaning compositions, including varying amounts of non-ionic surfactant and glycol ether (total amount of two actives is 6% by weight in all samples) as shown in Table 1, were prepared as follows: (1) 0.315% by weight Carbopol Ultrez 10 Polymer was mixed with water until hydrated; (2) Tomadol 91-6 was added; (3) Dowanol DPnB was added; (4) 3% by weight Microthene MN-722 was added; (5%) 1.15% by weight Kathon CG was added; and (6) 10% sodium hydroxide solution was added until a final pH of 6.5 was achieved. The solution was allowed to thicken. Two control compositions were also prepared. The first control composition included 6% by weight Dowanol DPnB with 0% by weight Tomadol 91-6, and the second control composition included 6% by weight Tomadol 91-6 and 0% by weight Dowanol DPnB.

TABLE 1

| | | Amount (wt %) | | | | | |
|---|---|---|---|---|---|---|---|
| Trade Name | Commercial Supplier | Cleaning Composition 1 | Cleaning Composition 2 | Cleaning Composition 3 | Cleaning Composition 4 | Cleaning Composition 5 | Cleaning Composition 6 |
| Carbopol Ultrez 10 Polymer | The Lubrizol Corporation (Wickliffe, Ohio) | 0.315 | 0.315 | 0.315 | 0.315 | 0.315 | 0.315 |
| Tomadol 91-6 ($C_{9-11}$ Pareth-6) | Air Products and Chemicals, Inc. (Allentown, Pennsylvania) | 1.0 | 3.0 | 4.0 | 4.5 | 4.8 | 5.0 |
| Dowanol DPnB (PPG-2 Butyl Ether) | The Dow Chemical Company (Midland, Michigan) | 5.0 | 3.0 | 2.0 | 1.5 | 1.2 | 1.0 |
| Microthene MN-722 (Polyethylene grit) | Equistar Chemical (Houston, Texas) | 3.0 | 3.0 | 3.0 | 3.0 | 3.0 | 3.0 |
| Kathon CG (5-chloro-2-methyl-4-isothiazolin-3-one and 2- | Rohm and Haas (Philadephia, Pennsylvania) | 1.150 | 1.150 | 1.150 | 1.150 | 1.150 | 1.150 |

TABLE 1-continued

| Trade Name | Commercial Supplier | Amount (wt %) | | | | | |
|---|---|---|---|---|---|---|---|
| | | Cleaning Composition 1 | Cleaning Composition 2 | Cleaning Composition 3 | Cleaning Composition 4 | Cleaning Composition 5 | Cleaning Composition 6 |
| methyl-4-isothiazolin-3-one) | | | | | | | |
| Sodium Hydroxide (10%) | Various suppliers | 1.150 | 1.150 | 1.150 | 1.150 | 1.150 | 1.150 |
| Water | — | Q.S. | Q.S. | Q.S. | Q.S. | Q.S. | Q.S. |
| Surface Cleaning Index (SCI) | — | 0.2 | 1 | 2 | 3 | 4 | 5 |

The tile samples were then labeled and placed on a scale. The scale was tared and then approximately 2 g of cleaning composition was applied to each square of each tile sample. The samples were then cleaned using the method detailed in Table 2 and as follows for the type of soil being analyzed:
(1) The area for cleaning was scrubbed aggressively for the time allotted using the pads of two fingers; and
(2) As the amount of scrubbing force was variable from person to person, it was recommended not to compare data from one person to that of another.

TABLE 2

| Soil Tested | Clean with 2 fingers for: | Side of Tile Cleaned |
|---|---|---|
| MGG | 15 seconds | Rough |
| Oil-Based Ink (OBI) | 30 seconds | Rough |

After cleaning, the cleaned area was then rinsed with running water and patted dry with a paper towel. The reflectance was measured using the reflectometer at two locations in the cleaned area ("cleaned" tiles).

The reflectometer measurements of the initial clean tiles (also referred to herein as "unsoiled" measurements of the tile samples), the reflectometer measurements of the soiled tiles, and the reflectometer measurements of the cleaned tiles were then used to calculate the percent soil removal by the cleaning composition. The percent soil removal (also referred to herein as "percent (%) cleaned") is calculated as follows:

% Cleaned=(Avg. Cleaned−Avg. Soiled)/(Unsoiled−Avg. Soiled)×100

Further, the amount of synergy using the sample cleaning compositions was determined. The synergy was calculated for each soil tested by the following method: (1) the cleaning performance of Tomadol 91-6 at a desired level (without Dowanol DPnB) in the sample composition was measured; and then (2) the cleaning performance of Dowanol DPnB (without Tomadol 91-6) in the composition was measured. For example, Tables 3A and 3B illustrate this for Cleaning Composition 2, wherein Baseline A composition was made with 3% Tomadol 91-6+0% Dowanol DPnB and Baseline B composition was made with 3% Dowanol DPnB+0% Tomadol 91-6. The cleaning performance of each of these compositions was then measured against MGG and ink soil. Then the Expected % Cleaned (also referred to herein, as "additive cleaning value") for the combination of these two compositions was calculated by adding the % Cleaned of Baseline A composition+% Cleaned of Baseline B composition. This was compared to the % Cleaned that was achieved with the composition containing both 3% by weight Tomadol 91-6 and 3% by weight Dowanol DPnB (Cleaning Composition 2 in this example). This allows the Individual Soil Synergy to be calculated by the following equation:

Individual Soil Synergy=(% Cleaned using Cleaning Composition 2)−(Expected % Cleaned)

Then the Combined Soil Synergy is calculated with the following equation:

Combined Soil Synergy=(Individual Soil Synergy with MGG)+(Individual Soil Synergy with Ink)

TABLE 3A

| Cleaning Composition | Baseline A Composition | Baseline B Composition |
|---|---|---|
| Carbopol Ultrez 10 Polymer | 0.315 | 0.315 |
| Tomadol 91-6 ($C_{9-11}$ Pareth-6) | 3.0 | 0.0 |
| Dowanol DPnB (PPG-2 Butyl Ether) | 0.0 | 3.0 |
| Microthene MN-722 (Polyethylene grit) | 3.0 | 3.0 |
| Kathon CG (5-chloro-2-methyl-4-isothiazolin-3-one and 2-methyl-4-isothiazolin-3-one) | 1.150 | 1.150 |
| Sodium Hydroxide (10%) | 1.150 | 1.150 |
| Water | Q.S. | Q.S. |

TABLE 3B

| | Baseline A Composition % Cleaned | Baseline B Composition % Cleaned | Expected % Cleaned | Cleaning Composition 2 Actual % Cleaned | Individual Soil Synergy | Combined Soil Synergy |
|---|---|---|---|---|---|---|
| MGG | 8.5 | 6.79 | 15.29 | 28.99 | 13.7 | 19.34 |
| Ink | 1.61 | 16.5 | 18.11 | 23.75 | 5.64 | |

Figure 2A:
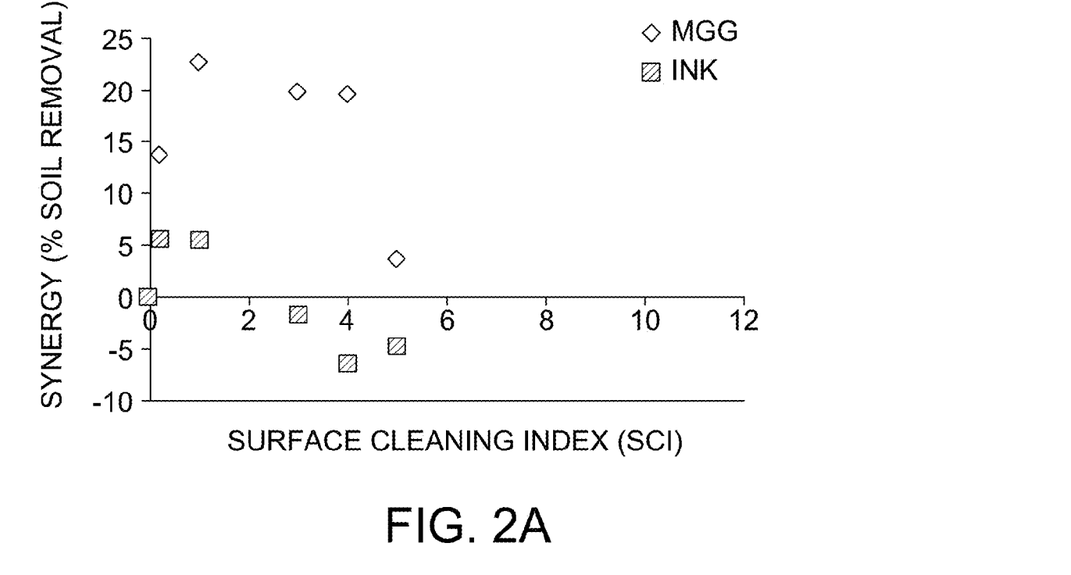
FIG. 2A is a graph depicting the component synergy using 6% by total weight non-ionic surfactant plus glycol ether solvent ("actives") as analyzed in Example 1.
Figure 2B:
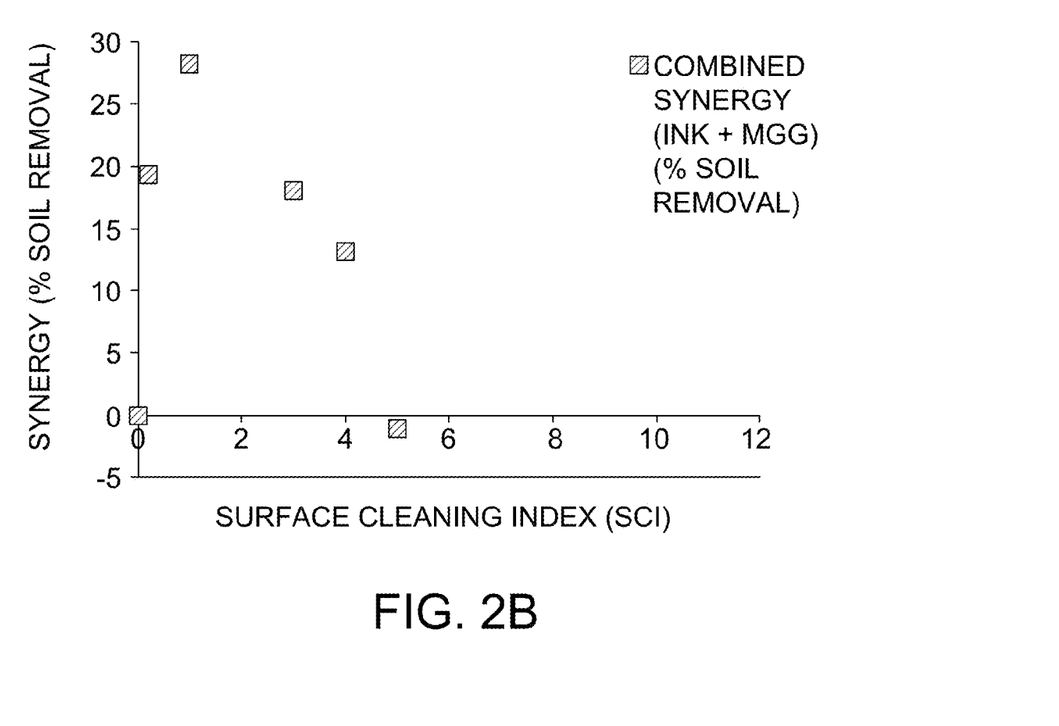
FIG. 2B is a graph depicting the combined synergy using 6% by total weight non-ionic surfactant plus glycol ether solvent ("actives") as analyzed in Example 1.

As shown in FIGS. 2A & 2B, it was surprisingly found that, in compositions that contained certain proportions of Tomadol 91-6 and Dowanol DPnB, improved cleaning was observed relative to that provided by the individual components. Specifically, when used in a surface cleaning index (SCI) of Tomadol 91-6 (non-ionic surfactant) to Dowanol DPnB (glycol ether) ranging from 0.2 to 4, the combination provided synergistic cleaning results for both the cleaning of MGG and ink. Further, when combined in a SCI of Tomadol 91-6:Dowanol DPnB of 5, there was synergistic cleaning of MGG.

This Example demonstrates the improved cleaning achieved by combining the non-ionic surfactant and glycol ether components in weight ratios such to provide a cleaning composition with the surface cleaning index as described herein.

Example 2

In this Example, the cleaning ability of various cleaning compositions of the present disclosure was analyzed. More particularly, this Example shows that alternate non-ionic surfactants show similar synergy affects as shown in Example 1.

Tiles were prepared and treated with MGG and OBI as described in Example 1. The cleaning compositions, as shown in Table 4, including 3% by weight non-ionic surfactant and 3% by weight glycol ether were prepared as follows: (1) 0.315% by weight Carbopol Ultrez 10 Polymer was mixed with water until hydrated; (2) 3% by weight non-ionic surfactant (Ethylan TD-60 (AkzoNobel Agrochemicals, Chicago, Ill.) or Lutensol® XP70 (BASF, Germany)) was added; (3) 3% by weight Dowanol DPnB was added; (4) 3% by weight Microthene MN-722 was added; (5%) 0.045% by weight Kathon CG was added; and (6) 10% sodium hydroxide solution was added until a final pH of 6.5 was achieved. The solution was allowed to thicken.

TABLE 4

| Trade Name | Commercial Supplier | Amount (wt %) Cleaning Composition 1 | Amount (wt %) Cleaning Composition 2 |
|---|---|---|---|
| Carbopol Ultrez 10 Polymer | The Lubrizol Corporation (Wickliffe, Ohio) | 0.315 | 0.315 |
| Ethylan TD-60 | AkzoNobel Agrochemicals (Chicago, Illinois) | 3.0 | — |
| Lutensol ® XP70 | BASF (Germany) | — | 3.0 |
| Dowanol DPnB (PPG-2 Butyl Ether) | The Dow Chemical Company (Midland, Michigan) | 3.0 | 3.0 |
| Microthene MN-722 (Polyethylene grit) | Equistar Chemical (Houston, Texas) | 3.0 | 3.0 |
| Kathon CG (5-chloro-2-methyl-4-isothiazolin-3-one and 2-methyl-4-isothiazolin-3-one) | Rohm and Haas (Philadephia, Pennsylvania) | 0.045 | 0.045 |
| Sodium Hydroxide (10%) | Various suppliers | 1.15 | 1.15 |
| Water | — | q.s. | q.s. |
| Surface Cleaning Index (SCI) | — | 1 | 1 |

The tiles were again cleaned with the cleaning compositions and the relevant baseline compositions, and reflectance were analyzed as described in Example 1. Results are shown in Table 5 below.

TABLE 5

| | Cleaning Composition 1 | | | | | |
|---|---|---|---|---|---|---|
| | Baseline A for Cleaning Composition 1 (3 wt % Ethylan TD-60 + 0 wt % Dowanol DPnB) | Baseline B for Cleaning Composition 1 (0 wt % Ethylan TD-60 + 3 wt % Dowanol DPnB) | Expected % Cleaned | Actual % Cleaned | Individual Soil Synergy | Combined Synergy |
| MGG | 29.4 | 6.2 | 35.6 | 76.2 | 40.6 | 46.15 |
| Ink | 1.25 | 21.4 | 22.65 | 28.2 | 5.55 | |

| | Cleaning Composition 2 | | | | | |
|---|---|---|---|---|---|---|
| | Baseline A for Cleaning Composition 2 (3 wt % Lutensol XP70 + 0 wt % Dowanol DPnB) | Baseline B for Cleaning Composition 2 (0 wt % Lutensol XP70 + 3 wt % Dowanol DPnB) | Expected % Cleaned | Actual % Cleaned | Individual Soil Synergy | Combined Synergy |
| MGG | 17.11 | 6.2 | 23.31 | 72.26 | 48.95 | 76.58 |
| Ink | 2.47 | 21.4 | 23.87 | 51.5 | 27.63 | |

As shown in Table 5, when the non-ionic surfactant and glycol ether were combined in a cleaning composition such to provide a SCI of 1, synergistic cleaning results for both the cleaning of MGG and ink were seen.

Example 3

In this Example, a cleaning composition of the present disclosure was analyzed for its cleaning ability. More particularly, this Example shows that alternate glycol ethers show similar synergy affects as shown in Example 1.

Tiles were prepared and treated with MGG and OBI as described in Example 1. The cleaning composition, including 3% by weight non-ionic surfactant (Tomadol 91-6) and 3% by weight glycol ether, was prepared as described in Example 2 with the exception of replacing Dowanol DPnB with the glycol ether, Dowanol Eph Glycol Ether (The Dow Chemical Company, Midland, Mich.). The cleaning composition is shown in Table 6.

TABLE 6

| Trade Name | Commercial Supplier | Amount (wt %) Cleaning Composition 1 |
|---|---|---|
| Carbopol Ultrez 10 Polymer | The Lubrizol Corporation (Wickliffe, Ohio) | 0.315 |
| Tomadol 91-6 | Air Products and Chemicals, Inc. (Allentown, Pennsylvania) | 3.0 |
| Dowanol Eph Glycol Ether | The Dow Chemical Company (Midland, Michigan) | 3.0 |
| Microthene MN-722 (Polyethylene grit) | Equistar Chemical (Houston, Texas) | 3.0 |
| Kathon CG (5-chloro-2-methyl-4-isothiazolin-3-one and 2-methyl-4-isothiazolin-3-one) | Rohm and Haas (Philadephia, Pennsylvania) | 0.045 |
| Sodium Hydroxide (10%) | Various suppliers | 1.15 |
| Water | — | q.s. |

TABLE 6-continued

| Trade Name | Commercial Supplier | Amount (wt %) Cleaning Composition 1 |
|---|---|---|
| Surface Cleaning Index (SCI) | — | 1.0 |

The tiles were cleaned with the cleaning composition, as well as the relevant baseline cleaning compositions, and reflectance were analyzed as described in Example 1. Results are shown in Table 7 below.

TABLE 7

| | Baseline A for Cleaning Composition 1 (3 wt % Tomadol 91-6 + 0 wt % Dowanol Eph) | Baseline B for Cleaning Composition 1 (0 wt % Tomadol 91-6 + 3 wt % Dowanol Eph) | Expected % Cleaned | Actual % Cleaned | Individual Soil Synergy | Combined Synergy |
|---|---|---|---|---|---|---|
| MGG | 13.30 | 9.60 | 22.90 | 67.47 | 44.57 | 79.94 |
| Ink | 1.73 | 10.10 | 11.83 | 47.20 | 35.37 | |

As shown in Table 7, when the non-ionic surfactant and glycol ether were combined in a cleaning composition such to provide a SCI of 1, synergistic cleaning results for both the cleaning of MGG and ink were seen.

Example 4

In this Example, the effect of the HLB of the non-ionic surfactant used in the cleaning composition on the cleaning ability of the cleaning composition was analyzed.

Cleaning compositions, having the base formulation shown in Table 8 and including 5% by weight of one of the non-ionic surfactants as shown in Table 9 below, were prepared as described herein.

TABLE 8

| Base Formulation | | |
|---|---|---|
| Trade Name | Commercial Supplier | Amount (wt %) |
| Carbopol Ultrez 10 Polymer | The Lubrizol Corporation (Wickliffe, Ohio) | 0.315 |
| Microthene MN-722 (Polyethylene grit) | Equistar Chemical (Houston, Texas) | 3.0 |
| Kathon CG (5-chloro-2-methyl-4-isothiazolin-3-one and 2-methyl-4-isothiazolin-3-one) | Rohm and Haas (Philadephia, Pennsylvania) | 0.045 |
| Sodium Hydroxide (10%) | Various suppliers | 1.15 |
| Water | — | q.s. |

TABLE 9

| Non-ionic Surfactant | Commercial Supplier | HLB | Avg. % Cleaning |
|---|---|---|---|
| Tomadol 91-2.5 | Air Products and Chemicals, Inc. (Allentown, Pennsylvania) | 8.5 | 53.5 |
| Tomadol 91-6 | Air Products and Chemicals, Inc. (Allentown, Pennsylvania) | 12.4 | 56.3 |
| Tomadol 91-8 | Air Products and Chemicals, Inc. (Allentown, Pennsylvania) | 13.9 | 13.0 |
| Tergitol 15-S-3 | The Dow Chemical Company (Midland, Michigan) | 8 | 16.9 |
| Tergitol 15-S-5 | The Dow Chemical Company (Midland, Michigan) | 10.5 | 52.1 |
| Tergitol 15-S-7 | The Dow Chemical Company (Midland, Michigan) | 12.1 | 31.9 |
| Tergitol 15-S-12 | The Dow Chemical Company (Midland, Michigan) | 14.5 | 11.0 |
| Tergitol 15-S-30 | The Dow Chemical Company (Midland, Michigan) | 17.4 | 12.5 |
| Lutensol XP30 | BASF (Germany) | 6.0 | 63.9 |
| Lutensol XP40 | BASF (Germany) | 8.0 | 72.0 |
| Lutensol XP70 | BASF (Germany) | 12.0 | 63.8 |
| Lutensol XP90 | BASF (Germany) | 14.0 | 19.4 |

The tiles were prepared and treated with MGG and cleaned with the cleaning compositions as described in Example 1. Further, percent cleaning of the cleaning compositions was analyzed as described in Example 1. The results are shown in Table 9 and in FIG. 3.

Figure 3:
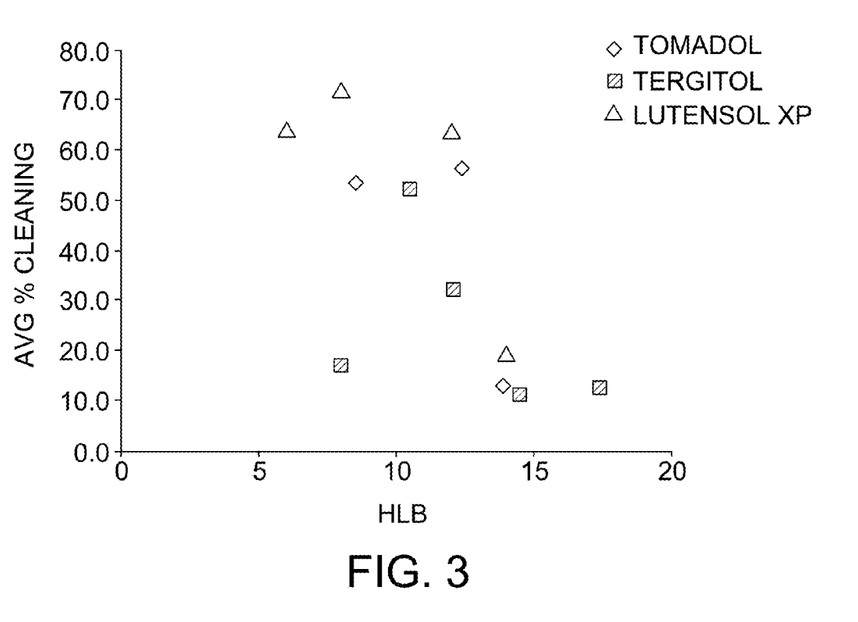
FIG. 3 is a graph depicting the average percent cleaning of surfactants as analyzed in Example 4.

As shown in Table 9 and in FIG. 3, non-ionic surfactants having HLB values between approximately 6 and 13 provide cleaning compositions having improved cleaning.

Example 5

In this Example, a suitable cleaning composition of the present disclosure was prepared. The components of the composition are shown in Table 10 below.

TABLE 10

| Trade Name | INCI Name | Amount (Wt %) | Commercial Supplier |
|---|---|---|---|
| Carbopol Ultrez 10 Polymer | Carbomer | 0.315 | The Lubrizol Composition (Wickliffe, Ohio |
| Tomadol 91-6 | $C_{9-11}$ Pareth-6 | 3 | Air Products and Chemicals, Inc. (Allentown, Pennsylvania |
| Dowanol DPnB | PPG-2 Butyl Ether | 4 | The Dow Chemical Company (Midland, Michigan) |
| d-Limonene | Limonene | 0.95 | Various suppliers |
| Mackamine LO | Lauramine Oxide | 8 | Rhodia (Bristol, Pennsylvania) |
| Microthene MN-722 | Polyethylene Grit | 3 | Equistar Chemical (Houston, Texas) |
| Dye | NA | 0.0212 | Sensient Technologies (St. Louis, Missouri) |
| Fragrance | NA | 0.19 | Alpine Aromatics (Piscataway, New Jersey) |

TABLE 10-continued

| Trade Name | INCI Name | Amount (Wt %) | Commercial Supplier |
|---|---|---|---|
| Sodium Hydroxide (10%) | Sodium Hydroxide | 1.15 | Various suppliers |
| Water | Water | Q.S. | — |

To prepare the cleaning composition, (1) carbomer was mixed with water until hydrated; (2) a 10 wt % solution of sodium hydroxide was added to reach a pH of approximately 6.5; (3) $C_{9-11}$ Pareth-6 was then added, followed by: (4) PPG-2 butyl ether; (5) d-limonene; and the remaining components listed in the table above.

Example 6

In this Example, a suitable cleaning composition of the present disclosure was prepared. The components of the composition are shown in Table 11 below.

TABLE 11

| Trade Name | INCI Name | Amount (wt %) | Commercial Supplier |
|---|---|---|---|
| Carbopol Ultrez 10 Polymer | Carbomer | 0.315 | The Lubrizol Corporation (Wickliffe, Ohio) |
| Tomadol 91-6 | $C_{9-11}$ Pareth-6 | 3 | Air Products and Chemicals, Inc. (Allentown, Pennsylvania) |
| Dowanol DPnB | PPG-2 Butyl Ether | 4 | The Dow Chemical Company (Midland, Michigan) |
| d-Limonene | Limonene | 0.95 | Various suppliers |
| Microthene MN-722 | Polyethylene grit | 3 | Equistar Chemical (Houston, Texas) |
| Sodium Hydroxide (10%) | Sodium Hydroxide | 1.15 | Various suppliers |
| Water | Water | Q.S. | — |

The cleaning composition was prepared using the following method: (1) carbomer was mixed with water until hydrated; (2) $C_{9-11}$ Pareth-6 was then added, followed by: (3) PPG-2 butyl ether; (4) d-limonene; (5) polyethylene grit; and finally, (6) 10% sodium hydroxide was added to reach a final pH of approximately 6.5.

Example 7

In this Example, a suitable cleaning composition for use in a wipe of the present disclosure was prepared. The components of the composition are shown in Table 12 below.

TABLE 12

| Trade Name | NCI Name | Amount (wt %) | Commercial Supplier |
|---|---|---|---|
| Tomadol 91-6 | $C_{9-11}$ Pareth-6 | 3 | Air Products and Chemicals, Inc. (Allentown, Pennsylvania) |
| Dowanol DPnB | PPG-2 Butyl Ether | 4 | Dow Chemical (Midland, Michigan) |
| d-Limonene | Limonene | 0.5 | Various suppliers |
| Calsoft AOS-40 | Sodium $C_{14-16}$ Olefin Sulfonate | 1.25 | Pilot Chemical (Middletown, Ohio) |
| Glycerin | Glycerin | 0.1 | Various suppliers |
| Citric Acid | Citric Acid | 0.225 | Various suppliers |
| Purox S | Sodium Benzoate | 0.45 | Emerald Kalama Chemical LLC (Kalama, Washington) |
| Bronidox 1160 | Phenoxythanol | 0.4 | BASF (Germany) |
| Water | Water | Q.S. | — |

The cleaning composition was prepared using the following method: (1) DPnB was premixed with d-limonene; (2) $C_{9-11}$ Pareth-6 was then added, followed by: (3) sodium $C_{14-16}$ olefin sulfonate; (4) water; (5) glycerin; (6) sodium benzoate; (7) phenoxyethanol; and finally, (8) citric acid was added to reach a final pH of approximately 4.75.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above cleaning compositions and cleansing products without departing from the scope of the disclosure, it is intended that all matter contained in the above description shall be interpreted as illustrative and not in a limiting sense.

What is claimed is:

1. A skin cleaning composition comprising a hydrolyzed plant protein and a synergistic combination of a non-ionic surfactant and a glycol ether, wherein the composition comprises from about 2% to about 5% of the non-ionic surfactant and from about 2% to about 4% of the glycol ether, and wherein the composition has a surface cleaning index of about 1.

2. The skin cleaning composition of claim 1 wherein the composition has a pH of from about 3 to about 8.

3. The skin cleaning composition of claim 1 wherein the non-ionic surfactant has an HLB value of from about 6 to about 13.

4. The skin cleaning composition of claim 1 wherein the glycol ether is selected from the group consisting of propylene glycol methyl ether, dipropylene glycol methyl ether, tripropylene glycol methyl ether, propylene glycol methyl ether acetate, dipropylene glycol methyl ether acetate, propylene glycol n-butyl ether, dipropylene glycol n-butyl ether, tripropylene glycol n-butyl ether, ethylene glycol phenyl ether, ethylene glycol n-butyl ether, diethylene glycol n-butyl ether, trimethylene glycol n-butyl ether, diethylene glycol methyl ether, trimethylene glycol methyl enantiomer, and combinations thereof.

5. The skin cleaning composition of claim 1 wherein the glycol ether is dipropylene glycol n-butyl ether.

6. The skin cleaning composition of claim 1 wherein the non-ionic surfactant is an alcohol ethoxylate.

7. The skin cleaning composition of claim 1 wherein the composition is substantially free of d-limonene.

8. A cleaning composition comprising a non-ionic surfactant, a glycol ether, and a hydrolyzed plant protein, wherein the non-ionic surfactant is present in an amount of less than 6% by weight of the composition, and wherein the composition has a surface cleaning index of about 1 and a pH of from about 3 to about 8.

9. The cleaning composition of claim 8 wherein the glycol ether is selected from the group consisting of propylene glycol methyl ether, dipropylene glycol methyl ether, tripropylene glycol methyl ether, propylene glycol methyl ether acetate, dipropylene glycol methyl ether acetate, propylene glycol n-butyl ether, dipropylene glycol n-butyl ether, tripropylene glycol n-butyl ether, ethylene glycol phenyl ether, ethylene glycol n-butyl ether, diethylene glycol n-butyl ether, trimethylene glycol n-butyl ether, diethylene glycol methyl ether, trimethylene glycol methyl enantiomer, and combinations thereof.

10. The cleaning composition of claim 8 wherein the non-ionic surfactant is an alcohol ethoxylate.

11. The cleaning composition of claim 8 wherein the composition is substantially free of d-limonene.

12. A wipe comprising a fibrous substrate and a skin cleaning composition, wherein the composition comprises a hydrolyzed plant protein and a synergistic combination of a non-ionic surfactant and a glycol ether, wherein the composition comprises from about 2% to about 5% of the non-ionic surfactant and from about 2% to about 4% of the glycol ether, and wherein the composition has a surface cleaning index of about 1.

13. The wipe of claim 12 wherein the glycol ether is selected from the group consisting of propylene glycol methyl ether, dipropylene glycol methyl ether, tripropylene glycol methyl ether, propylene glycol methyl ether acetate, dipropylene glycol methyl ether acetate, propylene glycol n-butyl ether, dipropylene glycol n-butyl ether, tripropylene glycol n-butyl ether, ethylene glycol phenyl ether, ethylene glycol n-butyl ether, diethylene glycol n-butyl ether, trimethylene glycol n-butyl ether, diethylene glycol methyl ether, trimethylene glycol methyl enantiomer, and combinations thereof.

14. The wipe of claim 12 wherein the non-ionic surfactant is an alcohol ethoxylate.

15. The wipe of claim 12 wherein the composition is substantially free of d-limonene.

16. The skin cleaning composition of claim 1 further comprising a skin conditioning agent.

17. The skin cleaning composition of claim 1 further comprising a thickener.

18. The skin cleaning composition of claim 17 wherein the thickener is selected from group consisting of acrylates, gums, cellulosics, starches, polyethylene glycols, and combinations thereof.

19. The skin cleaning composition of claim 1 wherein the composition comprises about 3% of the non-ionic surfactant and about 3% of the glycol ether.

20. The wipe of claim 12 wherein the composition comprises about 3% of the non-ionic surfactant and about 3% of the glycol ether.

* * * * *